US012636448B2

(12) United States Patent
Doemer et al.

(10) Patent No.: US 12,636,448 B2
(45) Date of Patent: *May 26, 2026

(54) VENTILATION DEVICE AND METHOD

(71) Applicant: Loewenstein Medical Technology S.A., Luxembourg (LU)

(72) Inventors: Benno Doemer, Ettlingen (DE); Ruediger Alshut, Karlsruhe (DE); Matthias Schwaibold, Karlsruhe (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 591 days.

This patent is subject to a terminal disclaimer.

(21) Appl. No.: 17/333,347

(22) Filed: May 28, 2021

(65) Prior Publication Data

US 2021/0283353 A1 Sep. 16, 2021

Related U.S. Application Data

(63) Continuation of application No. 15/626,281, filed on Jun. 19, 2017, now Pat. No. 11,027,079.

(30) Foreign Application Priority Data

Jun. 22, 2016 (DE) .......................... 102016007551.1

(51) Int. Cl.
*A61M 16/00* (2006.01)
*A61M 16/08* (2006.01)
(Continued)

(52) U.S. Cl.
CPC ........ *A61M 16/00* (2013.01); *A61M 16/0051* (2013.01); *A61M 16/022* (2017.08);
(Continued)

(58) Field of Classification Search
CPC .............. A61M 16/00; A61M 16/0051; A61M 16/022; A61M 16/0875; A61M 16/208;
(Continued)

(56) References Cited

U.S. PATENT DOCUMENTS 7,490,169 B1 * 2/2009 Ogdon .................... H04L 67/02
709/248
2003/0233129 A1 * 12/2003 Matos .................... G16H 40/63
607/5
(Continued)

FOREIGN PATENT DOCUMENTS

EP 1023912 A2 8/2000

OTHER PUBLICATIONS https://www.merriam-webster.com/dictionary/feedback (last accessed Jul. 12, 2025).*

*Primary Examiner* — Kendra D Carter
*Assistant Examiner* — Arielle Wolff
(74) *Attorney, Agent, or Firm* — Abel Schillinger, LLP

(57) ABSTRACT

The present invention relates to a method for operating a data processing unit of a ventilation device, and also to a ventilation device. Therapy data are registered and stored in a memory unit and at least a part of the therapy data is transmitted with a transmission unit to a network. At least one available radio network is determined with the transmission unit and at least one parameter for a network quality of the network is defined. At least one processing of the therapy data prior to their transmission into the radio network is carried out dynamically with the data processing unit depending on the parameter.

17 Claims, 2 Drawing Sheets

(51) Int. Cl.

| | |
|---|---|
| *A61M 16/20* | (2006.01) |
| *G16H 20/40* | (2018.01) |
| *G16H 70/20* | (2018.01) |
| *H04L 9/40* | (2022.01) |

(52) U.S. Cl.

CPC ..... *G16H 70/20* (2018.01); *A61M 2016/0027* (2013.01); *A61M 2016/003* (2013.01); *A61M 16/0875* (2013.01); *A61M 16/208* (2013.01); *A61M 2205/3584* (2013.01); *A61M 2205/3592* (2013.01); *A61M 2205/50* (2013.01); *A61M 2205/52* (2013.01); *G16H 20/40* (2018.01); *H04L 63/0428* (2013.01)

(58) Field of Classification Search

CPC .... A61M 2016/0027; A61M 2016/003; A61M 2205/3584; A61M 2205/3592; A61M 2205/50; A61M 2205/52; G16H 20/40; G16H 70/20; H04L 63/0428; H04W 48/18; H04W 48/00

See application file for complete search history.

(56) References Cited

U.S. PATENT DOCUMENTS

| | | | | |
|---|---|---|---|---|
| 2006/0159074 | A1* | 7/2006 | Diebold ............. | A61N 1/37252 |
| | | | | 370/352 |
| 2008/0253311 | A1* | 10/2008 | Jin ......................... | H04B 1/662 |
| | | | | 370/311 |
| 2015/0112264 | A1* | 4/2015 | Kamen ................ | A61B 5/0022 |
| | | | | 604/151 |
| 2016/0058962 | A1 | 3/2016 | Bychkov et al. | |
| 2017/0339676 | A1* | 11/2017 | Belghoul ............. | H04L 1/1861 |
| 2017/0359131 | A1* | 12/2017 | Mashimo ................ | H04L 69/14 |
| 2019/0192796 | A1* | 6/2019 | Schranz ............ | A61M 16/0051 |
| 2019/0366024 | A1* | 12/2019 | Feldhahn .......... | A61M 16/0051 |

* cited by examiner

VENTILATION DEVICE AND METHOD

CROSS-REFERENCE TO RELATED APPLICATIONS

The present application is a continuation of patent application Ser. No. 15/626,281, filed Jun. 19, 2017, which claims priority under 35 U.S.C. § 119 of German Patent Application No. 10 2016 007 551.1, filed Jun. 22, 2016. The entire disclosures of these applications are expressly incorporated by reference herein.

BACKGROUND OF THE INVENTION

1. Field of the Invention

The present invention relates to a method for operating a data processing unit of a ventilation device, and also a ventilation device with at least one data processing unit. Therapy data are registered and stored in at least one memory unit of the data processing unit. At least a part of the therapy data is transmitted with at least one transmission unit to a network.

2. Discussion of Background Information

Home ventilation devices or sleep therapy devices normally have a memory unit in order to be able to store and retrieve therapy data. Data which enable an individual adjustment of the ventilation device according to the respective needs of the user are therefore normally stored in the memory unit. This relates, for example, to the ventilation parameters necessary for the treatment of a specific respiratory disorder.

Furthermore, data which characterize the therapeutic process are also frequently stored. Such data are particularly helpful in order to be able to assess a success of the treatment or to support a specific diagnosis. Furthermore, the data also provide information indicating whether the user is using the ventilation device correctly and regularly.

A regular and as frequent as possible assessment of the therapy data is particularly important in order to be able to guarantee a reliable diagnosis and an effective treatment. The therapy data are normally evaluated during a visit by the carer. However, this has the disadvantage that no evaluation of the therapy data takes place between the visits. In addition, visits incur a substantial cost.

Ventilation devices which dial in to a mobile network via a GSM modem and thus transmit the therapy data to a network are therefore known. The therapy data can thereby be evaluated at a central location, independently from the location of the user and at any given time.

However, this transmission of the data has considerable disadvantages. Costs of a network operator are thus normally incurred for the transmission by means of a GSM modem. It has become evident in practice that these costs are often very unwelcome to both the user and the payer and, for example, an insurer.

It is furthermore disadvantageous that the transmission with a GSM modem is often very energy-consuming. This has a particularly disadvantageous effect in the case of ventilation devices with a mains-free battery operation. A further disadvantage is that users are often highly critical of the electromagnetic radiated power emanating from a GSM modem.

In view of the foregoing it would thus be advantageous to have available a method for operating a data processing unit of a ventilation device, and a ventilation device of this type, which enable an improved and in particular, a cost-optimized and/or energy-optimized transmission of therapy data to a network.

SUMMARY OF THE INVENTION

The present invention provides a method and a ventilation device as set forth in the instant independent claims. Refinements and advantageous designs thereof are the subject-matter of dependent claims.

The method according to the invention serves to operate a data processing unit of a ventilation device and, in particular, a home ventilation device and/or sleep therapy device. A ventilation device with a data processing unit can also be operated with the method. Therapy data are registered and stored in at least one memory unit of the data processing unit using the data processing unit. At least a part of the stored therapy data is transmitted with at least one transmission unit to at least one network. At least one available network is determined with the transmission unit. At least one parameter for a network quality of the radio network is defined with the transmission unit. At least one processing of the therapy data prior to their transmission into the radio network is carried out dynamically with the data processing unit depending on the parameter. As a result, a reliable and in particular, low-loss transmission of the therapy data is preferably possible, even in the case of a poorer network quality and, in particular, in the case of a connection to a low-energy, long-range network.

The method according to the invention has many advantages. A considerable advantage may be that a dynamic processing of the therapy data is carried out depending on the network quality. A reliable and secure transmission, even to radio networks with a restricted availability or transmission quality, is possible by means of such a processing of the therapy data. Radio networks which enable a cost-free or particularly low-cost and energy-optimized transmission of the therapy data can thereby also be used for the transmission. For example, due to the processing according to the invention, the therapy data can also be transmitted in low-energy, long-range networks (Low Power Wide Area Networks, LPWAN) or other cost-optimized and energy-optimized radio networks.

Since radio networks of this type impose requirements which differ substantially from those, for example, of the usual mobile networks or GSM networks, the processing of the therapy data is particularly crucial. For example, the requirement that the data volumes must be very compact can be met with the method proposed here. In addition, it can be guaranteed by the processing according to the invention that the forwarded therapy data also reach their respective destination in the radio network in complete form.

Since the usual mobile networks are optimized in terms of transmission speed and transmission volume, an adaptation of the therapy data depending on the network quality in radio networks of this type is not normally necessary. However, mobile networks of this type have the disadvantage that they are highly energy-consuming and incur an unwanted cost.

The parameter may preferably define an availability of the radio network. The parameter preferably defines a transmission reliability of the network. The parameter may, for example, describe a signal strength for this purpose. Other parameters which are suitable for a definition of the network quality are also possible. The therapy data can be particularly effectively processed using parameters of this type in order to guarantee a transmission that is as complete and reliable as possible.

It may also be possible for the parameter to describe at least one cost factor of the use of the radio network. A parameter of this type can be used particularly effectively for cost-optimized data transmission.

It may also be possible for the parameter to describe at least one measure of the energy requirement for a transmission into the network. A particularly targeted energy optimization of the transmission can be carried out depending on a parameter of this type. This is advantageous, for example, if the transmission is to take place independently from a mains power supply system.

With the transmission unit, at least a signal-to-noise ratio (SNR) and/or at least a signal strength in the uplink and/or downlink and/or at least an RSSI (Received Signal Strength Indicator) can particularly preferably be defined with the transmission unit as a parameter for the network quality. It may also be possible for the parameter to describe at least a result of a listen-before-talk query and/or an occupancy/traffic in the respective radio network.

At least one parameter for the network quality made available by the network operator can preferably be determined and used for the dynamic processing of the therapy data.

At least one of the network quality parameters listed below may preferably be defined with the transmission unit: link budgets, number of available and/or connected base stations of the radio network, distance to the nearest base station, noise levels and/or external signal source levels and/or channel occupancies in the transmission ranges, transmission latencies, parameters measured and/or calculated by the transmission unit and/or middleware/application servers and/or further system components, statistical parameters from previous transmissions, proportion and/or number of successful or failed connection and re-connection attempts, number of detected data packet collisions.

The parameter may also describe at least one transmission rate strength and/or transmission signal strength offered by the radio network or the low-energy, long-range network and/or demanded and/or negotiated. The parameter may also define anticipated interference levels and/or utilization levels, such as e.g. fluctuations at different times of the day.

The therapy data can preferably be prioritized for processing. The data volume to be transmitted can be substantially reduced and in particular, adapted to low-energy, long-range networks by means of a prioritization. In particular, the therapy data which exceed at least one threshold value for a priority are primarily and/or exclusively transmitted. According to the present invention, depending on the definition of a threshold value, it can also be provided that therapy data which fall below at least one threshold value for a priority are primarily and/or exclusively transmitted.

It may be possible for the priority to be allocated to the corresponding therapy data with consideration of a therapeutic and/or diagnostic function. For example, a higher priority can be allocated to a device parameter required for the desired ventilation. For example, a particularly high priority is allocated if the therapy data relate to the reliability of the treatment and/or the diagnosis. It is also possible for the priority to be allocated depending on the significance of the therapy data for an operational reliability of the ventilation device. The priority can also be allocated depending on the significance of the therapy data for a billing and/or proof of use. Date of this type are then preferably transmitted primarily and/or exclusively on the basis of a comparison of the priority with a threshold value.

The priority can particularly preferably be allocated depending on a change in the therapy data. For example, the time of a last change can be used for this purpose. As a result, unchanged data do not have to be transmitted and the data volume can thus be minimized accordingly. In addition, a particularly secure operation can thus be guaranteed, since changes in the therapy data can be immediately identified and taken into consideration in the therapy. By means of the data, it can thus be quickly established whether a user has made changes to the device configuration whether he or she responds differently to the ventilation.

A priority above the threshold value can particularly preferably be allocated to a number of therapy hours and/or a therapeutic process and/or a therapy statistic. In particular, a priority above the threshold value is allocated to a therapeutic process and/or a therapy statistic of the current and/or the previous day and/or the day most recently received by the network. In addition, it is also possible for data of this type to be transmitted with an increased redundancy. It is also possible for fault messages and/or error reports to be given a priority above the threshold value. Data of this type are particularly meaningful in assessing the therapy and/or making a diagnosis. A transmission can therefore be guaranteed through the increased priority, even in the case of a weaker radio network.

The threshold value for the priority can preferably be defined dynamically depending on the parameter. For example, the threshold value for the priority can be increased if the parameter defines a poor network quality. The therapy data which have a very high priority are then preferably transmitted primarily or exclusively. It is thus guaranteed that the available network quality is used exclusively or essentially for transmitting the important data. The threshold value is preferably reduced if the parameter defines a stable and high data transmission for the network. In such a case, lower-priority data, such as, for example, long-term statistical data, can then also be transmitted.

The therapy data can preferably be transmitted with a redundancy. The redundancy is preferably set dynamically depending on the parameter. In addition, the number of repetitions of the transmission of at least a part of the therapy data is set depending on the parameter. For example, a plurality of repetitions which are distributed over one day or over one week or over one month or a different time period can be provided. The therapy data are preferably transmitted redundantly at different times of the day and/or during a therapy. A redundant transmission in which the redundancy is set independently from the parameter can also be provided.

The repetitions are particularly preferably continued until at least one acknowledgement of receipt is received as a downlink from the network. It is also possible for the repetitions to be repeated independently from an acknowledgement of receipt. In particular, a maximum number of repetitions can be provided. The maximum number is preferably set dynamically depending on the parameter.

It may preferably be possible for one part of the therapy data to be transmitted with a higher redundancy than another part of the therapy data. Therapy data which exceed a threshold value for a priority are preferably transmitted with a higher redundancy. In particular, these therapy data are transmitted with a higher redundancy than therapy data which fall below a threshold value for a priority. Such a combination of priority and redundancy enables a particularly reliable transmission of important therapy data. In particular, the redundancy is adapted not only depending on the parameter for the network quality but also with consideration of the priority.

In one advantageous refinement, it can be specified, depending on the parameter, that the therapy data are transmitted via at least one network connection other than the radio network. The transmission unit then connects, in particular, via at least one GSM-based modem to at least one mobile network. The other network connection is, in particular, optimized for a transmission speed and for a data volume. The other network connection is preferably a radio network without an energy optimization, as is provided for the low-energy, long-range network.

A secure and reliable transmission of important data via the other network connection can thus be guaranteed if the network quality of the radio network is unfavorable. This is the case, for example, when a faster downlink is required for an operation of the ventilation device, for example in the event of a remote adjustment or a reconfiguration.

In addition, it may also be possible for the other network connection to be provided by at least one local network and, for example, a WLAN (Wireless Local Area Network) or LAN (Local Area Network). For example, the data are transmitted depending on the parameter via the local network to a network device of the patient and/or caregiver. The therapy data are, in particular, forwarded from there via a wide area network, for example to an evaluation unit for therapeutic and/or diagnostic analysis. This is done, for example, via the Internet, via a VPN and/or via a mobile communication connection. However, it is also possible for the therapy data to be transmitted directly via a wide area network which is not energy-optimized.

It may also be provided that the therapy data are stored on at least one storage medium and, in particular, on a transportable storage medium depending on the parameter. The transportable storage medium may, in particular, be disposed in the ventilation device in an exchangeable and/or removable manner. The storage medium may comprise e.g. a flash memory or be designed as such. This is advantageous, particularly in the case of very large data quantities. The storage medium can then be sent by post to a caregiver and/or to an evaluation unit.

A different alternative network connection which, in particular, is not energy-optimized, can offer a reliable facility for the fast transmission of larger data quantities also. Since a network connection of this type normally incurs higher costs and/or consumes more energy, this is preferably provided as fallback option in the case of an energy-optimized radio network with an unfavorable parameter. A cost-optimized selection is therefore preferably provided in which the other network connection and, for example, a GSM-based network connection are provided in exceptional cases only.

It may also be possible that the other network connection can preferably be used if a downlink and/or uplink with increased data volume is provided. This is the case, for example, when a software update and/or a new device configuration is to be transferred onto the ventilation device.

In one embodiment of the method, at least one remote adjustment facility of the ventilation device can be restricted and/or extended depending on the parameter. A remote adjustment facility is preferably restricted if the parameter defines a low network quality. A remote adjustment facility is preferably extended if the parameter defines a higher network quality. It is possible for the remote adjustment facility to be permanently and/or temporarily modified depending on the parameter. It is possible for at least one downlink to be transmitted by means of which the execution of the modification to the remote adjustment facility is instigated.

A remote adjustment facility is understood, in particular, to mean a framework within which the ventilation device is adjustable via at least one remote adjustment or telesetting. A remote adjustment is characterized, in particular, in that therapy data are transmitted from a location other than that of the ventilation device to the ventilation device, said therapy data effecting an adjustment of at least one device parameter and/or a modification to the device configuration and/or device software. Preferably, as a result of a restriction of the remote adjustment facility, remote adjustments can therefore only be made conditionally.

A high network quality is normally very important for a remote adjustment, since an incomplete transmission of the remote adjustment data can cause invalid or defective configurations. A restriction of the remote adjustment facility depending on the parameter can therefore guarantee a reliable operation.

If the remote adjustment facility is restricted, the ventilation device can fall back, in particular, on alternative device configurations in the memory unit. The therapy can thus be reliably carried out, at least partially independently from the remote adjustment. It is possible to wait until the parameter defines an improved network quality so that the remote adjustment facility is again extended.

It may be provided that at least one network connection other than the radio network is selected for the remote adjustment depending on the parameter. This is the case, for example, when a remote adjustment is required and the parameter indicates an inadequate network quality. A required device configuration and/or at least one device parameter, for example, can then be transmitted via the other network connection.

It may be possible for the parameter for the network quality of the network to be specified by at least one user input and/or by at least one remote adjustment. For example, the user can provide at least one location indication for the ventilation device, depending on which the parameter is specified. It is also possible for the location of use to be stored via at least one remote adjustment in the data processing unit. The location of use of the ventilation device can also be determined by the device itself, for example via a listening-in to the network (Listen Before Talk) and/or via reception a GPS signal. By means of indications of this type, the network quality available at the location of use can be particularly reliably determined and used as a parameter.

In all embodiments, it may be particularly preferable to transmit the parameter as at least one downlink to the ventilation device. In particular, the parameter may be transmitted as a downlink from at least one base station of the network to the ventilation device. This is particularly advantageous, since the parameter is frequently known to the network or to the base station. As a result, a technically complex determination of the parameter by the ventilation device can be dispensed with. It is possible for the parameter determined as a downlink to be converted by at least one algorithm into a parameter usable for the ventilation device.

The therapy data can preferably be checked for changes for processing. For this purpose, it is possible for the therapy data to be compared with at least one older or preceding data set which is stored in the memory unit. It is also possible for the therapy data to be checked for changes through comparison with therapy data which were determined in a preceding transmission to the network. For example, a comparison with an older file version can be provided.

Device configurations and/or device parameters and/or a therapeutic process are particularly preferably checked for changes. This is particularly advantageous, since device configurations or device parameters are normally relevant for an evaluation only if they have also been changed.

Therapy data with a data volume above a threshold value can preferably be transmitted via at least one network connection other than the radio network. This means, in particular, the volume of a coherent data packet and preferably of an uplink. It is also possible for therapy data with a data volume above a threshold value to be stored on at least one transportable storage medium. It can also be provided that therapy data with a priority above a threshold value are transmitted via at least one network connection other than the radio network.

It may particularly preferably be provided that therapy data to be received and, in particular, downlinks with a data volume above a threshold value are transmitted via at least one network connection other than the radio network. This is particularly advantageous for updates of device software and/or device configurations, since these normally have a high data volume. It can also be provided for updates of this type that a more up-to-date version of the device software and/or device configuration is stored on a transportable storage medium.

In one embodiment, it may be possible for an acknowledgement of receipt relating to the received therapy data to be forwarded by the radio network only after a predefined time period has elapsed. It is also possible for an acknowledgement of receipt relating to the received therapy data to be forwarded by the radio network only in conjunction with at least one further acknowledgement of receipt and/or at least one further downlink of therapy data. As a result, the number of acknowledgements of receipt to be forwarded can be substantially restricted, so that the data volume of the downlinks can be restricted.

Acknowledgements of receipt to be forwarded may particularly preferably be collected over a specific time period and can be forwarded as a bundle after a specific time period and/or when a specific quantity is reached. One advantageous optimization of the transmission volume also offers the linking of an acknowledgement of receipt to be forwarded with at least one other downlink. For example, an acknowledgement of receipt is linked with a device configuration which is to be forwarded and/or a device parameter.

In order to process the therapy data, at least one method step from a group of method steps can be carried out, said group comprising: data compression, restriction of at least one value range, differentiation and/or integration of absolute values. It is also possible for at least one bit mask to be applied. In addition, a prioritization and/or a check for changes is/are preferably carried out for the processing. Steps of this type offer a processing which particularly effectively meets the requirements for a transmission into a low-power, wide area network.

In one embodiment, at least one device parameter may be cumulatively counted. For example, the number of therapy hours is cumulatively counted. It is also possible for at least one user parameter to be cumulatively counted. A cumulative counting method offers substantial advantages over the use of indices, for example a daily hour counter. As a result, even in the absence of a transmission, for example in the event of poor network quality, an at least approximate estimation of the untransmitted data can be made. On the basis of a cumulative number of therapy hours, for example, an inference can be made regarding the hours of therapy in a period in which no data could be transmitted. Such a design of the ventilation device or the method is therefore particularly advantageous if the data are transmitted via a low-energy, long-range network.

The processing of the therapy data may preferably comprise at least one averaging. In particular, the therapy data of a time period in which an expected acknowledgement of receipt relating to the received therapy data has not been forwarded by the network are averaged by a processing. In a subsequent transmission, only the average value is then preferably transmitted for the corresponding therapy data. In particular, only the average value is then transmitted for a therapeutic process and/or a therapy statistic. A processing of this type offers the advantage that, following a lengthy time period without a reliable connection to the network, no unfavorably high data quantity occurs which has a high energy requirement or incurs substantial cost or blocks the transmission of other data.

A different targeted processing of the therapy data which compresses the data of this time period may also be possible. In particular, a statistical processing is provided in order to form only one or a smaller number of representative values from a group of values. It is also possible for a group of values to be described at least approximately by at least one function. The function is then preferably transmitted.

In all embodiments, it may be preferable for the transmission of the therapy data to be carried out even without feedback from the network. In particular, the transmission of the therapy data is carried out or continued even without an acknowledgement of receipt from the network. An operation of the ventilation device which is independent from the transmission of the therapy data is particularly preferably provided. An operation of the ventilation device even without the reception of a downlink by the network is preferably possible. As a result, on the one hand, the exploitation of the advantages of a network-based transmission is possible and, on the other hand, a reliable operation of the ventilation device is always guaranteed.

In one advantageous embodiment, the connection set-up of the transmission unit to the radio network may be carried out with a dynamic timing. In particular, the timing may be increased in a targeted manner for a remote adjustment of the ventilation device and/or for an initial therapy phase. It can thereby be ensured that the fastest possible connection set-up is carried out. The timing is preferably increased in a targeted manner for maximum latency. In particular, the therapy data may be transmitted following the connection set-up. The maximum latency is predefined, in particular, by at least one network protocol and/or at least one device configuration of the transmission unit.

It may be possible for the change in the timing also to be triggered by at least one user input. For example, the actuation of an operating unit is linked with an increase and/or decrease in the timing. This could occur, for example if the user selects a mode which requires a remote adjustment or for which a remote adjustment is helpful.

It may also be possible for the timing to be increased depending on a therapy mode, for example during a therapy mode for a critical respiratory condition. In other operating modes outside the remote adjustment and/or an initial phase of therapy, a reduced timing is preferably provided.

It may also be provided that at least one network connection other than the radio network is selected for a remote adjustment and/or for an initial therapy phase. A different network connection can be selected, for example, if even the timing increased for a maximum latency does not result in a successful connection set-up.

A connection between the ventilation device and a low-energy, long-range network may particularly preferably be initiated only by the ventilation device. This offers the advantage that the ventilation device or the transmission unit does not have to remain in a highly energy-consuming and costly receiving mode.

The connection set-up of the transmission unit to the radio network can be initiated by at least one downlink from at least one network connection other than the radio network. This is advantageous, since base stations of energy-optimized networks are often unable to initiate a connection set-up. The other network connection is therefore particularly helpful for an initiation of the connection from outside the ventilation device. For example, a connection set-up can be initiated by the other network connection if a device configuration or a remote adjustment is to be transmitted to the ventilation device. The subsequent transmission is preferably no longer carried out via the other network connection, but via the radio network. As a result, the energy and cost advantages of the low-energy, long-range network can nevertheless be exploited.

It may also be possible for the connection set-up of the transmission unit to the network to be initiated by at least one user input. The connection set-up may be initiated by means of a user input, for example, if the user has received a call or an SMS from a caregiver. However, it is also possible for a connection between the ventilation device and the low-energy, long-range network to be initiated by the low-energy, long-range network or from its base station also. The initiation may also be stored as a control command in a device configuration, so that an automatic initiation takes place during the operation of the ventilation device.

In all embodiments, it may be preferable for the operation and, in particular, a frequency selection of the transmission unit to be carried out with consideration of at least one regional specification of the radio network. The specification may preferably be determined by means of at least one method step from a group of method steps comprising: at least one carrier check on the receivable networks (Listen Before Talk), reception and evaluation of at least one GPS signal, evaluation of at least one GPS identifier of at least one base station of the network and or of a different network connection, consideration of at least one user input, consideration of at least one region-specific device configuration.

As a result, regional limitations may be particularly effectively identified and taken into consideration. This is particularly advantageous, since the requirements and regulations of low-energy, wide-area networks are regionally often very different. As a result, a trans-regional operation of the ventilation device is also reliably possible.

For example, the transmission of therapy data can be activated and/or deactivated with consideration of the regional specification. It may also be possible for at least one parameter to be specified for the transmission, such as e.g. a transmission frequency, transmission power, transmission time, behavior relating to Listen Before Talk or duty cycle. The setting of the transmission unit, for example, to unauthorized frequencies of a specific region can thereby be prevented. In particular, at least one network protocol from a group of network protocols is selected and/or set on the basis of the regional specification. The region-specific device configuration comprises, for example, at least one language setting and at least one selection of a time zone and/or at least one selection of a regional scheme.

It may be possible for the therapy data to be transmitted in at least partially encrypted form. For this purpose, at least one key may be provided which is preferably transmitted at least via a network connection other than the radio network. A particularly secure transmission of the therapy data is thereby possible. An end-to-end encryption, for example, is provided. In particular, the therapy data may be encrypted in relation to the network. It may be possible for the ventilation device to comprise at least one cryptochip. In particular, the key may be generated dynamically by the ventilation device and/or on the network side from information which is known, in particular, to both parties. Serial numbers and/or identification numbers and/or version identifiers, for example, may be used for this purpose. It is also possible for the key to be stored at least partially statically in the ventilation device. A plurality of encryption methods are particularly preferably combined with one another.

The transmission unit may comprise at least one modem unit. The modem unit is preferably identified at least during a first commissioning of the ventilation device. It is also possible for an identification of the modem unit to be carried out repeatedly. A stored network protocol is preferably selected on the basis of the identification. It may also be possible for a device configuration to be set on the basis of the identification. The device configuration may be set, for example, so that specific operating modes which are dependent on the transmission of therapy data by the modem unit are activated and/or deactivated.

A multiplicity of transmission units or modem units may be combined with a multiplicity of different types of ventilation devices by means of such a design of the method. The modem units can thus be selected in a targeted manner according to the specifications and facilities of low-energy, long-range networks without the ventilation devices having to undergo complex adaptations. By means of the identification during the commissioning, the ventilation device is then set in such a way that an optimum operation with the respective modem type is possible. A design of this type is furthermore particularly advantageous, since a multiplicity of different operators and regional specifications must be taken into consideration, particularly in the case of low-energy, long-range networks.

The transmission unit may be supplied with energy at least temporarily via at least one energy store. The energy store is preferably charged during an operation of the ventilation device. In particular, the energy store may comprise at least one capacitor. At least one Goldcap capacitor, for example, may be provided. This enables a transmission of therapy data which is independent from the power supply system of the ventilation device.

A design of this type can also be particularly advantageous if the ventilation device is mobile and is preferably equipped with a battery operation. A redundant transmission of therapy data, for example, can then be carried out throughout the entire day without the ventilation device having to be connected to the power supply system or without draining the battery.

In addition, a capacitor may be particularly advantageous as an energy store for transmission into a low-energy, long-range network. Networks of this type enable an energy-efficient transmission of data such that the energy of a corresponding capacitor is sufficient. An energy store of this type would not normally be sufficient for use in a GSM-based mobile network.

In all embodiments, it may be particularly preferable for at least one set from a group of data sets to be stored for the therapy data, said group comprising: recorded and/or set device parameters, recorded patient parameters, recorded and/or evaluated therapeutic processes, registered and/or evaluated therapy statistics, modifications and/or settings of device configurations, messages to the patient, error reports.

In all embodiments, it may furthermore be particularly preferable for a low-energy, long-range network and preferably a Low Power Wide Area Network (LPWAN) to be used to transmit the therapy data. A connection to at least one other network which is energy-optimized and/or cost-optimized compared with usual mobile networks may also be provided. Networks which are optimized for a low power consumption of the terminal devices, for a low data rate and for a long range and corresponding deep penetration, even of built-up areas, are preferably provided.

The transmission unit may be connected, in particular, to at least one base station of a low-energy, long-range network. Data may also be received via the connection to the low-energy, long-range network, in particular as a downlink. The therapy data are preferably forwarded from the low-energy, long-range network to an evaluation unit for therapeutic and/or diagnostic analysis.

With the transmission unit, a connection may also be set up via the network to at least one further ventilation device. As a result, a networking of two or more ventilation devices is preferably possible. The transmission unit can also set up a connection via the network to other telemetry units. Connections to other sensor networks and/or to the Internet of Things (IoT) are also possible.

In a different embodiment, the method may serve to operate a data processing unit of a ventilation device and, in particular, of a home ventilation device and/or sleep therapy device. Therapy data may be registered and stored in at least one memory unit of the data processing unit using the data processing unit. At least a part of the stored therapy data may be transmitted with at least one transmission unit to at least one network. At least one radio link to at least one network may be set up with the transmission unit. With the data processing unit, at least one processing of the therapy data may be carried out before their transmission into the network.

This method similarly offers many advantages, since the processing according to the invention of the therapy data enables a reliable data transmission, even to networks with a restricted availability or transmission quality. Low-energy, long-range networks and e.g. a Low Power Wide Area network (LPWAN) may thereby be used for transmission.

The ventilation device according to the invention comprises at least one ventilation unit for generating an airflow for a respiratory therapy. Therapy data can be registered using at least one data processing unit. The therapy data can be stored in at least one memory unit. At least one transmission unit is suitable and designed for transmitting at least a part of the stored therapy data to a network. The transmission unit is suitable and designed for determining at least one available network and to define at least one parameter for a network quality of the low-energy, long-range network. The data processing unit is furthermore suitable and designed for dynamically carrying out a processing of the therapy data before their transmission into the network depending on the parameter.

The ventilation device according to the invention also has many advantages. One particular advantage may be the data processing unit, so that the therapy data can be dynamically processed before their transmission into the network depending on the parameter. The ventilation device may thereby be used, for example, to transmit therapy data into a low-energy, long-range network.

The ventilation device is preferably suitable and designed for being operated using the method according to the invention. The transmission unit is, in particular, suitable and designed for being connected to at least one low-energy, long-range network and preferably a Low Power Wide Area network (LPWAN). In order to record the therapy data, the ventilation device preferably comprises at least one monitoring unit and/or at least one sensor unit.

BRIEF DESCRIPTION OF THE DRAWINGS

Further advantages and features of the present invention are set out in the description of the example embodiments, which are explained below with reference to the attached drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
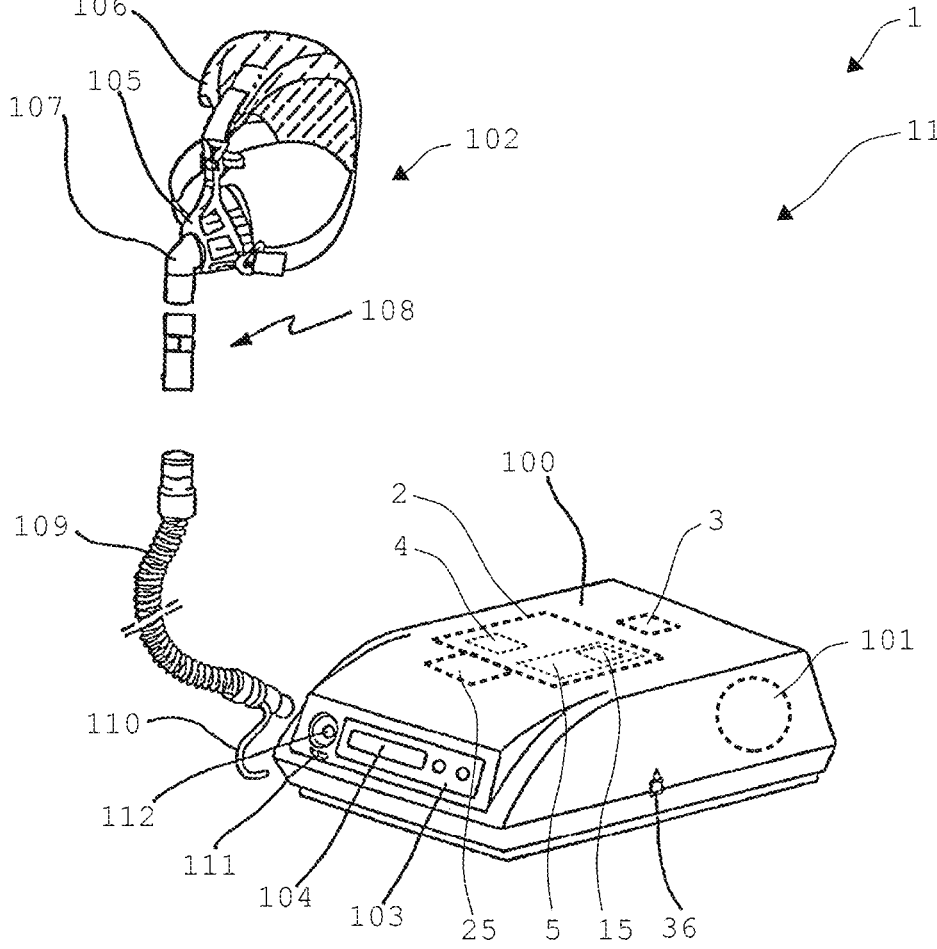
FIG. 1 shows a schematic representation of a ventilation device according to the invention in a perspective view.
Figure 2:
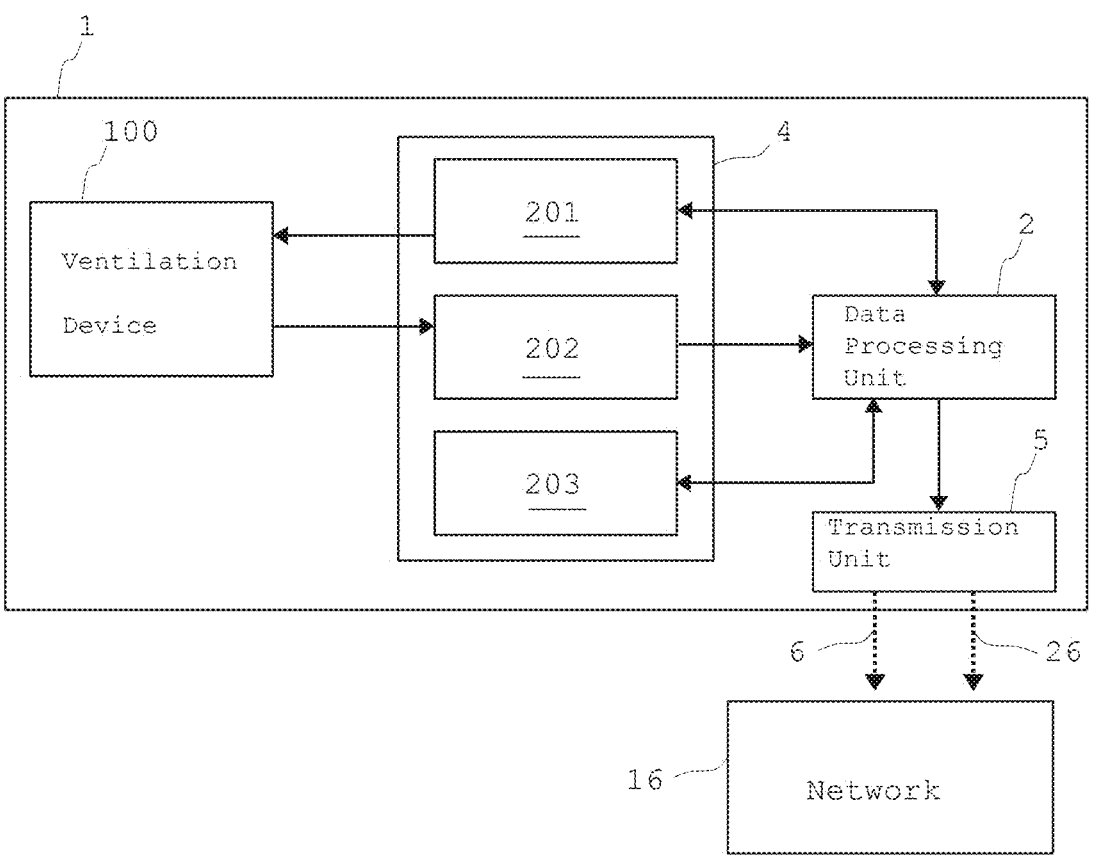
FIG. 2 shows a highly schematic representation of the ventilation device.

FIG. 1 and FIG. 2 show a ventilation device 1 which is designed as a home ventilation device 11 or sleep therapy device. However, the ventilation device 1 can also be used as a clinical ventilation device. The ventilation device 1 is suitable and designed for carrying out the method according to the invention.

The ventilation device 1 comprises a ventilation unit 100 with a fan unit 101 and one for generating an airflow for the ventilation. A monitoring unit 3 is provided here to control the ventilation unit 100 and to record therapy data. The operation and adjustment of the ventilation device 1 are carried out via an operating unit 103 with a display unit 104.

The ventilation device 1 has a respiratory interface 102 for feeding the airflow to a user for ventilation. The respiratory interface 102 is preferably designed as a patient interface and may be designed, for example, as a full-face mask, as a nasal pillow, as a tube or as a laryngeal mask. The respiratory interface 102 shown here is a respiratory mask 105 designed as a nasal mask. Headgear 106 is provided to attach the respiratory mask 105.

A connection tube 109 which is connected by means of a coupling unit 112 to the ventilation unit 100 is provided to connect the respiratory interface 102 to the ventilation unit 100. The ventilation tube 109 is connected to the respiratory interface 102 via a coupling element 107. An exhalation element 108 which comprises a valve or is designed as such is disposed between the ventilation tube 109 and the coupling element 107. The exhalation element 108 is provided, in particular, to prevent a rebreathing into the ventilation device 1 while the user exhales.

The monitoring unit 3 is operatively connected here to a sensor unit (not shown in detail) which has one or more sensors to record device parameters 201 and/or patient parameters and/or other parameters which are characteristic of the ventilation.

The monitoring unit 3 comprises, for example, a pressure sensor (not shown here in detail) which records the pressure conditions relating to the respiratory interface 102. The pressure sensor is connected via a pressure measurement tube 110 to the respiratory interface 102 for this purpose. The pressure measurement tube 110 is connected to the monitoring unit 3 via an inlet nozzle 111.

The monitoring unit 3 furthermore serves here to control the fan unit 101. The monitoring unit 3 provides a necessary minimum pressure and compensates for pressure fluctuations caused by the respiratory activity of the user. The monitoring unit 3 also records, for example, the prevailing pressure in the respiratory mask 105 and readjusts the power of the fan unit 101 accordingly until a desired respiratory pressure is applied. The device parameters 201 required in order to adjust the ventilation unit 100 or the fan unit 101, and also the device configuration and/or device software are stored in a memory unit 4.

The monitoring unit 3 can also be designed here to record patient parameters. For this purpose, the monitoring unit 3 can be equipped with sensors to measure the respiratory excursion, to measure a blood oxygen saturation and/or to measure an EEG, EMG, EOG or ECG activity.

The ventilation device 1 shown here may be designed as a fixed-level device or as an automatic-level device. In particular, an adjustment in line with reference device parameters 201 which have previously been individually calculated and specified on the basis of the characteristic breathing of a user is carried out by the monitoring unit 3.

It is also possible for the ventilation unit 100 to be adapted dynamically and, in particular, according to the respiratory phase of the user. For example, a respiratory phase change can be identified using the monitoring unit 3, so that a higher or lower pressure can be provided according to the respiratory phase. For example, the ventilation device 1 may be designed as a CPAP or APAP device. The ventilation device 1 may also be designed as a bilevel device. The ventilation device 1 responds, for example, to specific respiratory events, such as e.g. snoring, respiratory depression and/or obstructive pressure peaks with corresponding settings of the device parameters 201.

The pressure conditions recorded by the monitoring unit 3 are stored together with further device parameters 201 in a memory unit 4. In addition, the pressure conditions set by the monitoring unit 3 or the pressure adaptations that are carried out are similarly stored as device parameters 201 in the memory unit 4. The recorded patient parameters can also be stored in the memory unit 4.

For example, an initial therapy pressure, a maximum therapy pressure, a minimum therapy pressure and/or a target volume and/or other device parameters 201 suitable for setting the ventilation unit 100 can be stored as device parameters 201. These device parameters 201 are retrieved by the monitoring unit 3 from the memory unit 4 in order to set the ventilation unit 100.

The pressure conditions recorded over the therapy period and/or other device parameters and/or patient parameters in connection with therapeutic processes 202 are furthermore stored in the memory unit 4. A flow process, a pressure process and/or an event process, for example, can be registered as therapeutic processes 202. The therapeutic processes 202 are preferably supplied to the memory unit 4 by the monitoring unit 3 which records these data during the therapy.

The device parameters 201 and/or patient parameters and/or therapeutic processes stored in the memory unit 4 are retrieved here by a data processing unit 2 and are evaluated to produce one or more therapy statistics. The therapy statistic 203 is in turn stored in the memory unit 4. The therapy statistic 203 may be designed as a statistic in each case for a single therapeutic treatment. An average pressure and/or the therapy duration and/or a leakage parameter, for example, can be determined and stored.

The therapy statistic 203 may also be designed as a statistic in each case for one therapy period which comprises a plurality of therapeutic treatments. Averaged values for the average pressure and/or the therapy duration and/or the leakage parameter, for example, can be determined and stored. The therapy statistic 203 may also comprise an assessment of the user's willingness to cooperate.

The values and parameters stored in the memory unit 4 as previously described are referred to as therapy data in the context of the present invention. In order to be able to subject the therapy data to a therapeutic or diagnostic analysis or in order to be able to monitor the function of the ventilation device 1, a transmission of the therapy data to a network 16, e.g. via the Internet, is provided here. The network preferably comprises at least one server.

The therapy data can be accessed via the network 16 from a remote location, so that a location-independent evaluation is possible. The transmission is carried out by means of a transmission unit 5, wirelessly or via a radio link to a radio network 6. Here, the transmission unit 5 comprises a modem unit 15 for this purpose.

In addition to the transmission via the radio network 6, the therapy data can also be transmitted at least partially via a wireless and/or wired alternative network connection 26. In addition, the therapy data can also be stored at least partially on a storage medium 36. The storage medium 36 is designed, for example, as a memory card or a hard disk or a USB mass storage device.

An energy store 25 is provided here in order to enable a power supply of the transmission unit 5 which is temporarily independent from the mains power supply system. The energy store 25 is preferably charged during an operation in the mains power supply system. Here, the energy store 25 comprises one or more capacitors and, for example, Goldcap capacitors. A power supply of the transmission unit 5 lasting several hours or several days, for example, is provided.

The energy store 25 enables a particularly effective use of the low-power characteristics of low-energy, long-range networks. With a Goldcap capacitor, the data transmission can thus be extended over one day, even if the device 1 is removed from the power supply. To do this, either the complete protocol logic can be implemented in the modem 15, or transmit queues and receive buffers are implemented so that modems 15 can be used generically for many devices 1.

Here, the transmission unit 5 determines at least one parameter for a network quality of the available radio network 6. An availability and/or a transmission reliability of the radio networks 6, for example, is determined as a network quality. A signal strength of the radio network 6, for example, can be used for this purpose. The data processing unit 2 then carries out a processing of the therapy data which is adapted in a targeted manner according to the determined network quality parameter. The data processing unit 2 can also carry out a predefined processing of the therapy data so that the parameter no longer needs to be determined.

A low-energy, long-range network, and, particularly preferably, a Low Power Wide Area Network (LPWAN) is used here in order to minimize or reduce the transmission costs for the therapy data. The transmission costs per terminal and per annum are advantageously a fraction of the costs of GSM-based networks.

Radio networks 6 which communicate in licensed frequency ranges and/or license-free frequency ranges are possible. For example, LTE-M can be provided, which, compared with 3G LTE, has a significantly narrower bandwidth of 200 kHz and simplified protocols and modulation schemes which make fewer demands on processing capacity.

The transmission in license-free bands is carried out, in particular, at 868 MHz (Europe) and at 905-915 MHZ (USA) or according to the local regulations in other states. The data transmission rate is e.g. <100 bit/s (uplink, Europe). A data rate between 300 bit/s and 50 kbit/s is also possible. The data volume is restricted e.g. to 140 messages with a 12-byte payload from the device to the server (uplink) and, in particular, 4 messages with an 8-byte payload in the opposite direction (downlink). The downlink may preferably be set up only on the initiative of the terminal, i.e. a connection cannot be initiated by the server. However, transmission classes with time-pulsed downlink phases, i.e. with a guaranteed maximum latency and with a permanent downlink facility, are also possibly defined, so that a permanent two-way connection is possible.

The range is e.g. 3-10 km in urban areas and 30-50 km in rural areas, and also >1000 km in the case of a line-of-sight connection. The transmitted data are preferably available on central servers for retrieval. Data for the downlink can also be provided via these servers.

The method proposed here has the particular advantage that LPWAN networks 6 can be used in the transmission of the therapy data. Due to the dynamic data processing depending on the network quality of the radio network 6, a reliable transmission of the therapy data without relevant losses can thus be achieved via LPWAN networks 6 also.

A processing of the therapy data for their transmission in the LPWAN network 6 is described in detail below by way of examples.

The data volume transmittable in the LPWAN network 6 is normally strictly limited. The processing of the therapy data therefore preferably comprises a data compression. In particular, every bit is used and e.g. a bit mask is applied. The value ranges of the therapy data are restricted, in particular, to the maximum extent. For example, for the transmission of adjustment facilities for a soft start between 0 min and 45 min, in 5 min steps only 4 bits are provided for the 10 stages.

The therapy data are preferably prioritized so that only correspondingly important therapy data are transmitted. The allocated priorities are compared in relation to threshold values. The priorities are allocated, in particular, according to the significance of the data and preferably also with consideration of the network quality parameter.

In particular, differences rather than absolute values are transmitted. Values or data blocks are transmitted, in particular, only in the event of changes. Device settings or device configurations, for example, are transmitted only if they have changed.

The restrictions on the data volume normally apply to base stations and gateways also, since the available downlink time must be shared by all terminal devices connected to a gateway. Downlinks are also preferably processed and, in particular, limited as a result.

Acknowledgements of receipt or confirmations of transmission are dispatched, for example, only at defined intervals or only if useful data such as e.g. new device settings for the ventilation device 1 are also present. Data transmissions which require a larger data volume are preferably transferred onto parallel channels and preferably onto the other network connection 26. A detailed data upload is carried out, for example, via an upload program on the PC or smart device of the user or via a GSM-based modem or via the dispatch of a storage medium 36. The modem unit 15 is preferably designed for GSM-based transmission also. A firmware update can also be carried out by sending an SD card rather than via a downlink.

A transmission of the therapy data in the LPWAN network 6 may be disrupted at virtually any time by other applications which use the frequency band. The processing of the therapy data therefore comprises a protection against data loss.

The therapy data are preferably transmitted redundantly. The number of repetitions is specified, in particular, according to the significance of the data and preferably also with consideration of the network quality parameter. The therapy data are, for example, forwarded multiple times and also at different times of the day and, where appropriate, during therapy.

Cumulative counters instead of or in addition to indices are preferably used. In particular, operating hour counters are used instead of the counting of a daily usage. In particular, average values are transmitted for time periods for which the data transmission has not been confirmed. If, for example, no downlink has been received for one week or more, statistical average values for this week are transmitted when a downlink is again available.

Particularly important therapy data are preferably transmitted with high redundancy, less important therapy data with lower redundancy. In particular, an additional demand for data is provided. Checksums and hashes, in particular, are used.

In particular, a dynamic dependency between the redundancy and the scope of the data to be transmitted and the number of transmissions is set. Particularly cost-efficient transmission is thereby enabled. The network quality parameter, in particular, is also taken into consideration. If the network is e.g. weak and/or no response at all is received, basic data sets are preferably transmitted redundantly, e.g. number of therapy hours counter, basic statistics of the current therapy day or the previous day. If the network transmits reliably, the redundancy is withdrawn and the data scope can be extended.

In particular, a balance is struck between costs and data transmission reliability. The LPWAN 6 can thus be used in combination with the other network connection 26 and e.g. with conventional mobile radio communications. The other network connection 26 is preferably used if the LPWAN 6 is not adequate or data with increased volume requirements or security requirements are transmitted.

The network coverage is preferably taken into consideration in the adaptation of the ventilation device 1. A remote adjustment, for example, is thus blocked in a targeted manner if the downlink frequently or always fails to reach the device 1. An availability check can be carried out, for example on the basis of the network coverage. A location of use of the ventilation device 1 can be entered, and/or an expected connection quality. Usable services can then be output and, for example, the device configuration can be adapted on that basis.

A parameter 7 for a transmission quality for an uplink is normally stored in the radio network 6. The parameter 7 is therefore preferably transmitted to the ventilation device 1 in the downlink. The data forwarding can then be adapted on the device side depending on the notified parameter. For example, the redundancy is increased or the redundancy is reduced and the useful data scope is increased.

The processing and/or transmission of the therapy data take(s) account here of the fact that an asymmetric transmission may occur in the LPWAN network 6. The uplink, for example, is operational, but the downlink is not. According to the method proposed here, protocols which transmit data even without feedback from the server are therefore used. A targeted balance is struck between network occupancy and the number of messages and redundancy.

For example, specific therapy data with the highest priority are repeated n times, until a transition takes place to the forwarding of further therapy data. Since maximum uplink quality can be achieved by increasing the transmit power up to the permitted radiation limit even with a weak antenna, the application and the ventilation device 1 are preferably designed so that the downlink is deliberately dispensed with completely. This offers substantial cost benefits.

A terminal-device-initiated connection is preferably provided. If a guaranteed maximum latency is necessary, i.e. the device 1 is intended to connect to the radio network 6 within a defined time at the latest, e.g. for a remote adjustment or telesetting, the following method steps are preferably carried out. In particular, the connection set-up is timed for maximum latency, i.e. the device 1 registers with the radio network 6 at a defined time interval. This timing may also be dynamically variable, for example a maximum latency can be guaranteed during the normal office hours of the service providers, or in an initial therapy phase, and the timing is not provided/is reduced outside these hours.

The connection can also be initiated via the other network connection 26 or by a second channel, for example by means of an SMS to the device 1. A combined modem unit 15 for GSM 26 and LPWAN 6 is preferably provided for this purpose. An operating element which the user can press as required can also be provided on the device 1 for the connection set-up.

The regionally appropriate and permitted frequency range is preferably selected and further regional regulations are preferably taken into consideration in the transmission of the therapy data.

A country-specific parameterization is preferably switchable and/or selectable by region-specific modems. An automatic switchover or activation or deactivation of the radio modules can be carried out via various mechanisms. In particular, the regional specification of the radio network 6 is determined.

For example, a carrier check (Listen Before Talk) is carried out. It can also be determined whether there are indications of LPWAN networks 6 in the radio ether, e.g. by means of beacons. A GPS signal of a built-in receiver can also be used. A GPS identifier of the base station can also be used if at least one of the networks 6, 26 is received. A user input which defines the region of use can also be used. Settings of the ventilation device 1, such as e.g. language, regional scheme, time zone, can also be used to determine the region of use.

The processing of the therapy data comprises, in particular, an encryption and authentication, e.g. AES, RSA. For example, an end-to-end encryption is provided so that data are encrypted in relation to the radio network 6. The key is generated either dynamically on the device and server side or from information which is known to both sides or is stored statically in the device 1.

Serial numbers or other identification numbers or version identifiers, for example, can be used for this purpose. In particular, a plurality of methods are combined with one another for the encryption. A cryptochip can be used for sensitive information. In particular, the information from which the key is generated is not or at least not regularly transmitted via the radio network.

The LPWAN-based networks 6 normally represent a highly heterogeneous system in which many providers and many different components prevail. The modem unit 15 is therefore identified during a first commissioning of the ventilation device 1 and a stored network protocol is selected and/or a device configuration is set on the basis of the identification. The manufacturing cost can thus be kept low despite the variety of requirements.

In addition, web interfaces to different providers and/or adaptation modules are preferably produced. The business and application logic behind these modules is as identical as possible for the relevant manufacturers. A logistics infrastructure which enables the identification, activation, deactivation and allocation of modems 15 and devices 1 in production, in supply logistics and in operation for the various radio networks 6 is thus achieved. For example, the ventilation device 1 polls the modem 15 and selects the behavior and protocol according to the modem type.

REFERENCE NUMBER LIST

1 Ventilation device
2 Data processing unit
3 Monitoring unit
4 Memory unit
5 Transmission unit
6 Radio network
7 Parameter
11 Home ventilation device
15 Modem unit
16 Network
25 Energy store
26 Network connection
36 Storage medium
100 Ventilation unit
101 Fan unit
102 Respiratory interface
103 Operating unit
104 Display unit
105 Respiratory mask
106 Headgear
107 Coupling element
108 Exhalation element
109 Ventilation tube
110 Pressure measurement tube
111 Inlet nozzle
112 Coupling unit
201 Device parameter
202 Therapeutic process
203 Therapy statistics

What is claimed is:

1. A method for operating a data processing unit of a ventilation device, wherein the method comprises registering therapy data and storing them in at least one memory unit of the data processing unit and transmitting at least a part of the stored therapy data with at least one transmission unit to at least one network, wherein at least one available radio network is determined with the transmission unit, at least one parameter for a network quality of the radio network is defined, and at least one processing of the therapy data prior to their transmission into the radio network is carried out dynamically with the data processing unit depending on the at least one parameter, and wherein an acknowledgement of receipt relating to received therapy data is forwarded by the radio network only after a predefined time period has elapsed and/or only in conjunction with at least one further acknowledgement of receipt and/or at least one further downlink of therapy data.

2. The method of claim 1, wherein the at least one parameter defines an availability and/or a transmission reliability of the radio network.

3. The method of claim 1, wherein the therapy data are transmitted with a redundancy which is set dynamically depending on the at least one parameter.

4. The method of claim 1, wherein it is specified depending on the at least one parameter that the therapy data are transmitted via at least one network connection other than the radio network.

5. The method of claim 1, wherein at least one remote adjustment facility of the ventilation device is restricted and/or extended depending on the at least one parameter.

6. The method of claim 1, wherein the at least one parameter is transmitted as at least one downlink to the ventilation device.

7. The method of claim 1, wherein therapy data with a data volume above a threshold value are transmitted via at least one network connection other than the radio network and/or are stored on at least one transportable storage medium.

8. The method of claim 1, wherein at least one of: data compression, restriction of at least one value range, differentiation of absolute values is carried out for the processing of the therapy data.

9. The method of claim 1, wherein therapy hours are cumulatively counted and transmitted as at least one device parameter.

10. The method of claim 1, wherein the therapy data are transmitted even without feedback from the radio network.

11. The method of claim 1, wherein a connection set-up of the transmission unit to the network is carried out with a dynamic timing, and wherein the timing is increased in a targeted manner for a remote adjustment of the ventilation device and/or for an initial therapy phase.

12. The method of claim 1, wherein a connection set-up of the transmission unit to the radio network is initiated by at least one downlink to the ventilation device from a network connection other than the radio network and/or is initiated by at least one user input.

13. The method of claim 1, wherein an operation of the transmission unit is carried out with consideration of at least one regional specification of the radio network, and wherein the specification is determined on the basis of at least one of: at least one carrier check (Listen Before Talk), reception and evaluation of at least one GPS signal, evaluation of at least one GPS identifier of at least one base station, consideration of at least one user input, consideration of at least one region-specific device configuration.

14. The method of claim 1, wherein the therapy data are transmitted in at least partially encrypted form.

15. The method of claim 1, wherein the transmission unit comprises at least one modem unit which is identified at least during a first commissioning of the ventilation device, and wherein a stored network protocol is selected and/or a device configuration is set on the basis of the identification of the modem unit.

16. The method of claim 1, wherein the transmission unit is supplied with energy at least temporarily via at least one energy store which is charged during an operation of the ventilation device.

17. The method of claim 1, wherein at least one data set from a group of data sets is stored for the therapy data, which group comprises: recorded and/or set device parameters, recorded patient parameters, recorded and/or evaluated therapeutic processes, registered and/or evaluated therapy statistics, modifications and/or settings of device configurations, messages to the patient, error reports.

* * * * *